US012644832B2

(12) United States Patent
Rothwell

(10) Patent No.: US 12,644,832 B2
(45) Date of Patent: Jun. 2, 2026

(54) SYSTEMS AND METHODS FOR SPECTRAL ANALYSIS OF PLANTS

(71) Applicant: Terramera, Inc., Vancouver (CA)

(72) Inventor: Austin Caulfield Rothwell, Vancouver (CA)

(73) Assignee: TERRAMERA, INC., Vancouver (CA)

( * ) Notice: Subject to any disclaimer, the term of this patent is extended or adjusted under 35 U.S.C. 154(b) by 214 days.

(21) Appl. No.: 18/268,127

(22) PCT Filed: Dec. 17, 2021

(86) PCT No.: PCT/CA2021/051830
§ 371 (c)(1),
(2) Date: Jun. 16, 2023

(87) PCT Pub. No.: WO2022/126277
PCT Pub. Date: Jun. 23, 2022

(65) Prior Publication Data
US 2024/0044785 A1      Feb. 8, 2024

Related U.S. Application Data

(60) Provisional application No. 63/127,813, filed on Dec. 18, 2020.

(51) Int. Cl.
*G01N 21/3563*      (2014.01)
*G01J 3/28*          (2006.01)
(Continued)

(52) U.S. Cl.
CPC ........ *G01N 21/3563* (2013.01); *G01J 3/2823* (2013.01); *G01N 21/31* (2013.01);
(Continued)

(58) Field of Classification Search
None
See application file for complete search history.

(56)                References Cited

U.S. PATENT DOCUMENTS 6,008,492 A      12/1999  Slater et al.
6,587,575 B1     7/2003   Windham et al.
(Continued)

FOREIGN PATENT DOCUMENTS

WO       2019173606 A1     9/2019
WO       2020159913 A1     8/2020
(Continued)

OTHER PUBLICATIONS

Bhosle et al. "Red Edge Point Detection for Mulberry Leaf", (2017).
(Continued)

*Primary Examiner* — Edwin C Gunberg
(74) *Attorney, Agent, or Firm* — Roni M. Jones; Oyen Wiggs Green & Mutala LLP

(57)                ABSTRACT

Systems and methods for hyperspectral imaging of plants are provided. Multispectral images of plants are transformed, e.g. by interpolation along a spectral axis, to generate hyperspectral images of plants. The transformation can be based on spectral bases formed from hyperspectral sample images including images of plant matter. Plant characteristics, such as plant health, may be predicted based on the hyperspectral image. Plant health may be predicted by comparing derivatives of reflectance values with respect to wavelength for a plant of a given image relative to a reference derivative based on a reference hyperspectral image. The derivatives may be compared by determining a regression loss.

19 Claims, 8 Drawing Sheets

(51) Int. Cl.

| | |
|---|---|
| *G01N 21/31* | (2006.01) |
| *G01N 21/359* | (2014.01) |
| *G01N 21/84* | (2006.01) |
| *G01N 33/00* | (2006.01) |

(52) U.S. Cl.

CPC ...... *G01N 21/84* (2013.01); *G01J 2003/2826* (2013.01); *G01N 21/359* (2013.01); *G01N 2021/8466* (2013.01); *G01N 33/0098* (2013.01); *G01N 2201/1296* (2013.01)

(56) References Cited

U.S. PATENT DOCUMENTS

| | | | |
|---|---|---|---|
| 6,639,665 | B2 | 10/2003 | Poole |
| 6,646,264 | B1 | 11/2003 | Modiano et al. |
| 7,058,197 | B1 | 6/2006 | McGuire et al. |
| 7,715,013 | B2 | 5/2010 | Glaser et al. |
| 7,835,002 | B2 | 11/2010 | Muhammed et al. |
| 8,563,934 | B2 | 10/2013 | Yao et al. |
| 9,551,616 | B2 | 1/2017 | McQuilkin et al. |
| 10,408,748 | B2 | 9/2019 | Schwartzer et al. |
| 10,951,831 | B2 | 3/2021 | Seiffert et al. |
| 2006/0006335 | A1 | 1/2006 | Lawrence et al. |
| 2007/0065857 | A1 | 3/2007 | Glaser et al. |
| 2008/0144013 | A1 | 6/2008 | Lanoue et al. |
| 2010/0073504 | A1 | 3/2010 | Park et al. |
| 2013/0094717 | A1 | 4/2013 | Janni et al. |
| 2014/0093138 | A1 | 4/2014 | Naganuma et al. |
| 2014/0122044 | A1 | 5/2014 | Yasukawa |
| 2016/0202679 | A1* | 7/2016 | Bermudez Rodriguez ................. G05B 19/042 700/284 |
| 2017/0251134 | A1 | 8/2017 | Zhang |
| 2019/0056314 | A1 | 2/2019 | Aalders et al. |
| 2019/0096049 | A1 | 3/2019 | Kim et al. |
| 2019/0219499 | A1 | 7/2019 | Gold et al. |
| 2019/0236358 | A1 | 8/2019 | Tokumaru |
| 2019/0277749 | A1 | 9/2019 | Rushing et al. |
| 2020/0334458 | A1 | 10/2020 | Glenn |
| 2024/0044785 | A1 | 2/2024 | Rothwell |

FOREIGN PATENT DOCUMENTS

| | | |
|---|---|---|
| WO | 2020232298 A1 | 11/2020 |
| WO | 2022126276 A1 | 6/2022 |
| WO | 2022126277 A1 | 6/2022 |

OTHER PUBLICATIONS

Moshou et al. "Intelligent multi-sensor system for detection and treatment of fungal diseases in arable crops", (2011).

Siok et al., "A simulation approach to the spectral quality of multispectral images enhancement", (2020).

Han et al. (2011) Fast Spectral Reflectance Recovery Using DLP Projector, Computer Vision—ACCV 2010. Lecture Notes in Computer Science, vol. 6492. doi:10.1007/978-3-642-19315-6_25.

Haneishi et al, Applied Optics (13 pages). Available at least as early as Dec. 17, 2021.

Haneishi et al. System design for accurately estimating spectral reflectance of art paintings. Department of Information and Image Science, Chiba University. Available at least as early as Dec. 17, 2021.

Park et al. Multipsectral Imaging Using Multiplexed Illumination. Conference Paper in Proceedings / IEEE International Conference on Computer Vision. IEEE International Conference on Computer Vision. Jan. 2007. DOI: 10.1109/ICCV.2007.4409090. Source: DBLP.

Parkkinen et al., Characteristic spectra of munsell colors, Journal of the Optical Society of America A 6 (1989) 318-322.

Xie et al., MHF-Net: An Interpretable Deep Network for Multispectral and Hyperspectral Image Fusion. IEEE, Aug. 11, 2020, vol. 44(3), pp. 1457-1473.

* cited by examiner

600

602

604

Processor(s)

606

Communication Interface

608

Storage Device(s)

610

Operating System — 614

Multispectral Engine — 616

Interpolation Engine — 618

Prediction Engine — 620

Spectral Bases — 622

Calibration Settings — 624

Images — 626

...

Other Applications and Data — 630

Input / Output Device(s) — 612

SYSTEMS AND METHODS FOR SPECTRAL ANALYSIS OF PLANTS

CROSS-REFERENCE TO RELATED APPLICATIONS

This application is a 371 national phase entry of Patent Cooperation Treaty application No. PCT/CA2021/051830 filed 17 Dec. 2021 entitled SYSTEMS AND METHODS FOR SPECTRAL ANALYSIS OF PLANTS, which claims priority to, and the benefit of, U.S. provisional patent application No. 62/127,813 filed 18 Dec. 2020 and entitled Systems and Methods for Hyperspectral Imaging of Plants. Each of the foregoing applications are incorporated herein by reference for all purposes in their entireties.

TECHNICAL FIELD

The present disclosure relates generally to machine vision, and in particular to spectral analysis of plants.

BACKGROUND

Multispectral and hyperspectral imaging involves capturing light across a plurality of spectral bands. For instance, hyperspectral images are sometimes referred to as "hyperspectral cubes" to reflect their (typically) two spatial dimensions (e.g. corresponding to a two-dimensional array of pixels) and their spectral dimension (corresponding to various wavelengths, sometimes binned as "channels"). A multi- or hyperspectral image may have tens, hundreds, or even thousands of channels. Multi- and hyperspectral imaging have found applications in agriculture and other plant-related disciplines to analyze plant characteristics, such as plant health. Such applications may make use of plants' spectral characteristics which are not readily distinguishable in a conventional RGB image.

For example, multi- and hyperspectral images have been used to determine characteristics of plants, such as detecting the presence of plant matter and/or distinguishing between healthy and unhealthy plants. Such approaches typically make use of the spectral characteristics of healthy plants (and/or portions of plants), which tend to have more reflectance intensity in certain wavelengths relative to unhealthy plants and/or non-plant objects. See, for example, U.S. Pat. No. 7,715,013. A variety of measures of relative reflectance are used, of which the most common is normalized differential vegetation index (NDVI), which can be expressed as (NIR−red)/(NIR+red), where NIR is reflectance measured in near-infrared wavelengths (where healthy plants tend to have high reflectance) and red is reflectance in red wavelengths (where healthy plants tend to have limited reflectance). Plants with a high NDVI value can be predicted to be more likely to be healthy than those with lower NDVI values. See, for example, US Patent Publication No. 2019/0236358.

There is a general desire for techniques for making use of multi- and/or hyperspectral images to determine characteristics of plants.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides a system and method for hyperspectral characterization of plants. The system comprises one or more processors and a memory storing instructions which cause the one or more processors to perform operations according to the method. The method comprises receiving a hyperspectral image comprising a number m of hyperspectral channels, at least one hyperspectral channel comprising an infrared wavelength, the hyperspectral image representing at least a portion of at least one plant; generating a determination for the at least the portion of at least one plant based on the hyperspectral image based on a derivative of a plurality of reflectance values of the hyperspectral image with respect to wavelength.

In some embodiments, the determination comprises a prediction of plant health and generating the determination comprises determining the prediction of plant health based on the derivative of the plurality of reflectance values and a plurality of reference reflectance values.

In some embodiments, the method comprises generating the plurality of reference reflectance values based on a reference hyperspectral image representing at least a healthy portion of a reference plant. In some embodiments, generating the plurality of reference reflectance values comprises determining an average of reflectance values for a plurality of spatial locations of the at least the healthy portion of the reference plant for each of a plurality of the n hyperspectral channels.

In some embodiments, determining the prediction of plant health comprises determining a difference between the derivative of the plurality of reflectance values and a derivative of the plurality of reference reflectance values with respect to wavelength. In some embodiments, determining the difference comprises determining a regression loss metric based on the derivative of the plurality of reflectance values and a derivative of the plurality of reference reflectance values. In some embodiments, the regression loss comprises at least one of: a mean square error, a mean absolute error, a Huber loss, a log-cosh loss, and a quantile loss.

In some embodiments, the plurality of reference reflectance values comprise a first plurality of reference reflectance values corresponding to at least a first portion of at least a first plant and a second plurality of reference reflectance values corresponding to at least a second portion of at least a second plant, the first and second portions differing in at least one of: species of plant, type of disease, type of damage, and degree of damage.

In some embodiments, determining the prediction of plant health comprises: determining a first prediction of plant health based on the derivative of the plurality of reflectance values and the first plurality of reference reflectance values; determining a second prediction of plant health based on the derivative of the plurality of reflectance values and the second plurality of reference reflectance values; and selecting the first prediction based on the first prediction corresponding to a greater likelihood of health than the second prediction.

In some embodiments, the spectral bases having been generated from one or more images comprising at least one image representing at least a further portion of at least one further plant. In some embodiments, the plurality of spectral bases comprises at least four spectral bases.

In some embodiments, generating the hyperspectral image comprises interpolating at least one hyperspectral reflectance value for a wavelength of at least one of the n hyperspectral channels outside of the m multispectral channels.

In some embodiments, the method further comprising segmenting the multispectral image into plant and non-plant regions; wherein generating the hyperspectral image comprises generating the hyperspectral image for the plant regions.

In some embodiments, the method further comprises: receiving an input multispectral image comprising a number m of input multispectral channels, at least one multispectral channel comprising an infrared wavelength, the multispectral image representing at least a portion of at least one plant; and generating the multispectral image comprising a number n of multispectral channels based on the input multispectral image and a plurality of spectral bases, the number n of multispectral channels greater than the number m of input multispectral channels.

In some embodiments, the spectral bases having been generated from one or more images comprising at least one image representing at least a further portion of at least one further plant. In some embodiments, the plurality of spectral bases comprises at least four spectral bases.

In some embodiments, generating the multispectral image comprises interpolating at least one multispectral reflectance value for a wavelength of at least one of the n multispectral channels outside of the m input multispectral channels.

In some embodiments, the method comprises segmenting the input multispectral image into plant and non-plant regions; wherein generating the multispectral image comprises generating the multispectral image for the plant regions.

In some embodiments, the method comprises: receiving a calibration input multispectral image representing at least a portion of a calibration subject, the at least the portion of the calibration subject substantially non-reflective in one or more input multispectral channels of the m input multispectral channels; and determining, for at least one of the one or more input multispectral channels, a corresponding calibration reflectance of at least a portion of the input multispectral image representing at least the portion of the calibration subject; wherein generating the multispectral image comprises, for the at least one of the one or more input multispectral channels, subtracting the corresponding calibration reflectance.

In some embodiments, at least one of the m input multispectral channels comprises at least one wavelength in a range of about 525 nm to 575 nm. In some embodiments, at least one of the m input multispectral channels comprises at least one wavelength in a range of about 600 nm to 700 nm. In some embodiments, at least one of the m input multispectral channels comprises at least one wavelength in a range of about 400 nm to 500 nm. In some embodiments, the m input multispectral channels comprise at least four input multispectral channels. In some embodiments, the m input multispectral channels comprise no more than ten input multispectral channels.

In some embodiments, receiving the input multispectral image comprises causing an imaging sensor having infrared sensitivity to capture one or more frames through one or more optical filters. In some embodiments, the imaging sensor comprises at least one of: an RGB imaging sensor with NIR sensitivity and a monochrome imaging sensor; the one or more optical filters comprise a plurality of optical filters; and causing the imaging sensor to capture one or more frames comprises causing the imaging sensor to capture a plurality of frames by capturing at least one frame through each of the plurality of optical filters. In some embodiments, causing the imaging sensor to capture the plurality of frames by capturing at least one frame through each of the plurality of optical filters comprises causing the plurality of optical filters to revolve through a field of view of the imaging sensor while causing the imaging sensor to capture frames.

In some embodiments, generating the determination comprises: determining, for a first spatial location of at least one of the input multispectral image and the multispectral image, that a measure of one or more reflectance values of the first spatial location at least one of: exceeds a specularity threshold and is less than non-illumination threshold; and excluding the one or more reflectance values of the first spatial location from the determination based on said determining.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

One aspect of the present disclosure relates to generating determinations about plants from multispectral images (which may comprise hyperspectral images). For instance, plant health can be predicted by comparing derivatives of reflectance values with respect to wavelength for a plant of a given hyperspectral image relative to a reference derivative based on a reference hyperspectral image (e.g. of a healthy plant). The derivatives may be compared, for example, based on a difference between the derivatives, e.g. by determining a regression loss. Such techniques may, in suitable circumstances, provide more accurate characterization of healthy vs. unhealthy plants (by making use of more complete spectral information to characterize plants' spectral response), and/or provide improved consistency between illumination intensities. This aspect includes an example apparatus for capturing multi- and/or hyperspectral images.

Figure 1:
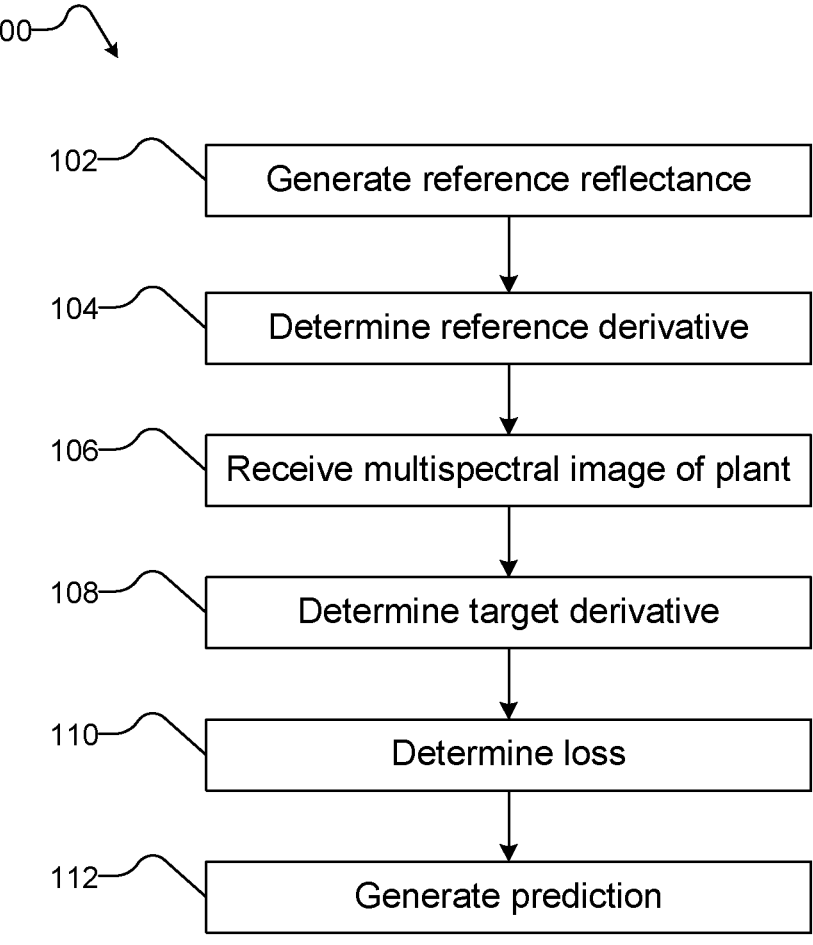
FIG. 1 is a flowchart illustrating an example method for generating hyperspectral images based on multispectral images.

A Method for Generating Determinations from Spectral Characteristics of Plants FIG. 1 is a flowchart illustrating an example method 100 for characterizing plants based on their spectral characteristics. Method 100 is performed by a computing system, as described elsewhere herein (e.g. with reference to FIG. 6). The method involves determining a derivative of the plant's reflectance with respect to wavelength. Plant spectral characteristics in multispectral images tend to be strongly affected by illumination and other factors, whereas plant spectral characteristics tend to be less affected by such factors in the first derivative (and higher-order derivatives). Characterization of plants may comprise, for example, predicting plant health based on such a derivative of plant spectral characteristics.

Method 100 may be performed based on an image representing at least a portion of a plant having sufficient spectral channels to determine a derivative with respect to wavelength (e.g. with respect to channels). Such number of wavelengths/channels may be 3, 4, 5, 6, 7, 8, 9, 20, 50, 100, 100, 500, 1000, any number therebetween, and/or any greater number. The image may thus conventionally be thought to be hyperspectral or multispectral. For convenience, the following disclosure may occasionally refer to such an image processed according to the systems and methods disclosed herein as a "multispectral image" without the intent of limiting such images to non-hyperspectral embodiments. The image may have any suitable number of spatial dimensions, such as zero (e.g. as may be the case for images produced by a spectrometer), one, or two. The multispectral image may be obtained in any suitable way, e.g. it may be predetermined, acquired from a imaging system (e.g. a multi- and/or hyperspectral imaging system), generated from another multispectral and/or hyperspectral image (e.g. as described elsewhere herein), and/or otherwise obtained.

Method 100 involves determining a derivative of reflectance values with respect to wavelength (which may comprise, for example, determining a derivative of reflectance values with respect to the image's spectral channels) to characterize the plant. The computer system may, for example, compare that derivative to a reference, such as a derivative of a reference reflectance generated from a reference multispectral image of a (healthy) reference plant, and may generate a prediction based on that comparison. The reference multispectral image may comprise the same spectral channels as multispectral images processed by method 100.

The reference may be predetermined, generated by the computer system as part of method 100, and/or otherwise obtained. For example, in at least the depicted embodiment, at act 102, the computing system generates a reference reflectance based on a reference multispectral image representing (at least a portion of) a reference plant. The reference plant (and/or a portion thereof) may be a healthy plant, thereby providing a reference for the spectral characteristics of a healthy plant. Generating the reference reflectance may comprise, for example, determining a reflectance value for each of a plurality of wavelengths (and/or channels) of the reference multispectral image. Such determining may comprise, for example, selecting the reflectance value from a predetermined spatial location (e.g. a center of the image, a center of mass of the representation of the plant, etc.), determining a measure of a plurality of reflectance values (e.g. the maximum, minimum, median, average, or other measure of reflectance values), and/or any other suitable determination.

In some embodiments, act 102 comprises determining an average reflectance for a plurality of spatial locations (e.g. pixels) of the reference multispectral image representing the plant. For instance, the computing system may optionally segment the multispectral image to classify regions of the multispectral image as representing plant or non-plant (e.g. background) objects. (Such segmentation may be alternatively or additionally be predetermined.) Any suitable segmenting method may be used; for example, the computing system may classify plants as foreground and non-plants as background based on Otsu thresholding. In some embodiments, the computing system performs segmentation based on one frame of the multispectral image (e.g. a frame captured through a shortpass filter covering some or all of the visible spectrum, and/or a frame comprising a conventional RGB image to facilitate segmentation by available segmentation models) and may apply that segmentation mask to all frames of the multispectral image. Subsequent acts based on the multispectral image, such as determinations at act 104 and/or 110, may be limited to portions of the multispectral image classified as plant. The computing system may determine an average reflectance of all spatial locations (e.g. pixels) classified as "plant". In some embodiments, the computing system applies morphological adjustments to reduce the likelihood of including non-plant objects in plant-labelled regions, such as by applying binary closing and/or binary erosion.

In some embodiments where the computing system determines a measure of a plurality of reflectance values, the computing system excludes from its determination (e.g. excludes from the average) one or more spatial locations based on specularity and/or non-illumination. For example, experimentation has shown that prediction of plant health can be unreliable in areas with significant specularity, such as in the case of the highly reflective leaves of cabbage plants, and/or in areas covered by shadow where a plant's natural reflectance may not be visible due to a lack of light. In some embodiments, the computing system excludes spatial locations (e.g. pixels) with an average reflectance across one or more (e.g. all) channels of a multispectral image which is greater than a specularity threshold. In some embodiments, the computing system excludes spatial locations with an individual measure of reflectance (e.g. an average reflectance) across one or more (e.g. all) channels of a multispectral image which is less than a non-illumination threshold. For example, the computing system may determine an average reflectance value for a given channel based only on pixels which have an average reflectance across all channels which do not exceed the specularity threshold and which do exceed the non-illumination threshold. Such an approach may be particularly advantageous in hyperspectral imaging embodiments by making use of relatively dense spectral information available to draw inferences about the spectral characteristics of specific spatial locations, but may also be advantageously applied in at least some multispectral imaging embodiments, in suitable circumstances.

In some embodiments, act 102 comprises generating a reference reflectance based on a plurality of reference multispectral images. For example, the computing system may generate a reflectance for each channel of each image (e.g. as described above) and may average or otherwise combine such reflectance values to generate the reference reflectance. For example, the computing system may average the reflectance values of a plurality of images of healthy plants to generate the reference reflectance.

In some embodiments, act 102 comprises generating a plurality of reference reflectance values. For example, act 102 may generate a first reference reflectance for a plant (or plants, and/or portions thereof) of a first species, and may generate a second reference reflectance for another plant (or plants, and/or portions thereof) of a second species. Alternatively, or in addition, the computing system may generate different reference reflectance values for images of different organs of plants (e.g. for leaves and for stems, optionally for the same species), for different health statuses (e.g. for healthy plants and unhealthy plants), for different types of disease (e.g. for *Sclerotinia* and for powdery mildew), for different types of damage (e.g. for disease, for breakage, and/or for malnourishment), for different degrees of damage (e.g. for severe disease and for mild disease), and/or for other distinctions between plants and/or portions thereof.

In some embodiments, method 100 involves comparing a derivative of reflectance for a multispectral image with a derivative of reflectance for a reference multispectral image. The derivative of reflectance for the reference multispectral image may be predetermined, generated by the computer system as part of method 100, and/or otherwise obtained. For example, method 100 may comprise act 104, which comprises determining a derivative of the reference reflectance with respect to wavelength. This may include, for example, determining a derivative with respect to the spectral channels of the reference multispectral image and/or with respect to the channels/wavelengths of another multispectral image (e.g. by estimating, interpolating, or otherwise generating spectral values corresponding to the channels/wavelengths of the multichannel image received at act 106). The derivative may be calculated in any suitable way, including by discrete methods (such as those provided by the numpy scientific library), by continuous methods (e.g. by fitting discrete reference reflectance values to a curve and determining the derivative of the curve), and/or by any other suitable method.

At act 106, the computing system receives a multispectral image representing at least a portion of at least one plant. The multispectral image comprises an image representing at least a portion of a plant having sufficient spectral channels to determine a derivative with respect to wavelength (e.g. with respect to channels). Such number of wavelengths/channels may be 3, 4, 5, 6, 7, 8, 9, 10, 20, 50, 100, 100, 500, 1000, any number therebetween, and/or any greater number. Act 106 may comprise receiving the multispectral image from a user, accessing a predetermined multispectral image, generating the multispectral image by the computing system, and/or otherwise obtaining the multispectral image.

At act 108, the computing system determines a derivative of reflectance with respect to wavelength for the multispectral image received at act 106. This may include, for example, obtaining reflectance values for the multispectral image (and/or of a plant and/or of a portion thereof represented by the image) substantially as described with reference to act 102 and determining a derivative of the reflectance values with respect to the spectral channels of the multispectral image substantially as described with reference to act 104. In some embodiments, the computing system also or alternatively determines the derivative with respect to channels/wavelengths corresponding to another multispectral image, for instance by estimating, interpolating, and/or otherwise generating spectral values corresponding to the channels/wavelengths of the reference multichannel image. The derivative may be calculated in any suitable way, including by discrete methods (such as those provided by the numpy scientific library), by continuous methods (e.g. by fitting discrete reference reflectance values to a curve and determining the derivative of the curve), and/or by any other suitable method.

In some embodiments, at act 110, the computing system compares the reflectance values for the plant of the multispectral image with the reference reflectance values. In some embodiments, such comparison comprises comparing the derivative of reflectance values of act 108 (called the "target derivative" or ds herein) with the derivative of reference reflectance values of act 104 (called the "reference derivative" or dr herein). Such comparisons may comprise, for example, determining a difference between the target derivative and the reference derivative. In at least one example embodiment, act 110 comprises determining a regression loss metric based on the target derivative and the reference derivative. For instance, act 110 may comprise determining a mean square error of the target derivative relative to the reference derivative over n channels $\lambda_i$, which may be expressed as:

$$MSE\left[\frac{ds}{d\lambda}, \frac{dr}{d\lambda}\right] = \frac{1}{n}\sum_{i=1}^{n}\left(\frac{ds}{d\lambda}(\lambda_i) - \frac{dr}{d\lambda}(\lambda_i)\right)^2$$

Alternatively, or in addition, act 110 may comprise determining a mean absolute error between the target derivative and the reference derivative, a Huber loss between the target derivative and the reference derivative, a log-cosh loss between the target derivative and the reference derivative, a quantile loss between the target derivative and the reference derivative, and/or any other suitable regression loss metric between the target derivative and the reference derivative.

In some embodiments, act 110 comprises a plurality of comparisons. For example, in an embodiment where the computing system has a plurality of reference reflectance values (e.g. having generated such reference reflectance values at act 104 and/or otherwise obtained such reference reflectance values), the computing system may perform comparisons as described above between the target derivative and a derivative for each of the reference reflectance values with respect to wavelength.

At act 112, the computing system generates a determination for the (at least a portion of a) plant represented in the multispectral image of act 106 based on the target derivative. In at least some embodiments, the computing system generates the determination based on the comparison of act 112. In some embodiments, the determination comprises a prediction of plant health. For example, the computing system may determine that a regression loss metric value exceeds a threshold and, based on such determination, may predict that the plant is not healthy. Alternatively, or in addition, the computing system may bin regression loss metric values into various categorical bins (e.g. "healthy", "partially healthy", "unhealthy"). Alternatively, or in addition, the computing system may provide a predicted healthiness score based on the regression loss metric (e.g. as a heatmap of regression metric values). For instance, the computing system may provide the regression loss metric as a healthiness score for regression loss metric values below the threshold and may group regression loss metric values above the threshold as 100% unhealthy.

The computing system may generate predictions for specific spatial locations (e.g. pixels), for regions of a multispectral image (and thus regions of the represented plant), and/or for an entire multispectral image and/or plant. For example, where a multispectral image comprises representations of multiple plants, the computing system may segment the plants (or otherwise identify each plant) and generate a plurality of predictions for each spatial location (e.g. pixels) representing portions of that plant.

The computing system may optionally generate a combined prediction for the plant by combining the plurality of predictions for each spatial location representing portions of that plant. For instance, the computing system may generate an average regression loss metric, and/or may score each spatial location for the given plant characteristic (e.g. plant health) as described herein and provide an area-based measure for that characteristic. For example, for a leaf which has one healthy half and one diseased half, the computing system may generate a prediction for each spatial location representing that leaf (e.g. as heatmap), and/or may generate a prediction comprising an average regression loss metric for the leaf (and may, e.g., generate a prediction based on such average regression loss metric as described herein), and/or may generate a prediction comprising measure of how much of the leaf is "healthy" and/or "diseased" (e.g. based on one or more thresholds for healthy and/or diseased predictions) as a proportion of the visible area.

In some embodiments where the computing system has received a plurality of reference reflectance values (e.g. varying by species, disease, or other factors, as described elsewhere herein), the computing system generates a first determination for the (at least a portion of a) plant based on the target derivative and a first reference derivative, and generates a second determination for the (at least a portion of a) plant based on the target derivative and a second reference derivative. (It will be understood that more than two determinations may be generated.) The computing system may select one of the predictions based on which of the predictions corresponds to the highest confidence, smallest regression loss, and/or the greatest likelihood of health. As one example, if the first prediction corresponds to a "healthy" prediction and the second prediction corresponds to an "unhealthy" prediction, the computing system may select the first prediction. As another example, if the first prediction corresponds to a healthy reference plant and the second prediction corresponds to an unhealthy reference plant (e.g. one displaying significant disease), a low regression loss metric value for the second prediction may indicate a high confidence that the plant is unhealthy and the computing system may select the second prediction.

In some embodiments, the computing system receives an indication associating a set of one or more plants with one of a plurality of references. For example, the computing system may receive a multispectral image at 106 representing a corn field and may receive an indication that the multispectral image comprises representations of corn plants. Such indication may be predetermined, provided by a user, generated by the computing system (e.g. according to a classification machine learning model executed by the computing system and trained over images of various species of plants), and/or otherwise suitably obtained. The computing system may select a reference derivative based on the indication (e.g., in the foregoing example, the computing system may select a reference derivative based on a reference multispectral image of healthy corn) and may generate a prediction based on target derivative and the selected reference derivative as described elsewhere herein without necessarily performing a comparison between the target derivative and one or more unselected reference derivatives.

In some embodiments, the computing system alternatively or additionally generates a prediction of plant species, type of disease, type of damage, and/or degree of damage based on a comparison between the target derivative and a reference derivative, and in particular based on the plant species, type of disease, type of damage, and/or degree of damage (as appropriate) of the reference plant corresponding to the most-similar (e.g. lowest-loss) reference derivative. For instance, if the first prediction corresponds to a reference plant comprising wheat and the second prediction corresponds to a reference plant comprising corn, a low regression loss metric value (e.g. lower than a threshold, and/or lower than a regression loss metric value for the first prediction) may indicate a high confidence that the target plant (i.e. the plant corresponding to the target derivative) is corn, and the computing system may generate such a prediction on that basis.

In some embodiments, method 102 comprises receiving a multispectral image at act 102. In some embodiments, method 102 comprises generating a multispectral image at act 102 based on an input multispectral image, the generated multispectral image comprising more wavelengths (e.g. more spectral channels) than the input multispectral image. Generating more spectrally-dense representations of plant images may assist in the performance of determinations and generation of predictions of method 100. An example method for generating such multispectral images is provided below and also in U.S. Patent Application No. 63/127,813, incorporated by reference in its entirety and for all purposes.

Figure 2:
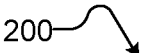
FIG. 2 is a flowchart illustrating an example method for characterizing plants based on reflectance values of a hyperspectral image, such as a hyperspectral image generated according to the method of FIG. 1 (or otherwise obtained).
Figure 2:
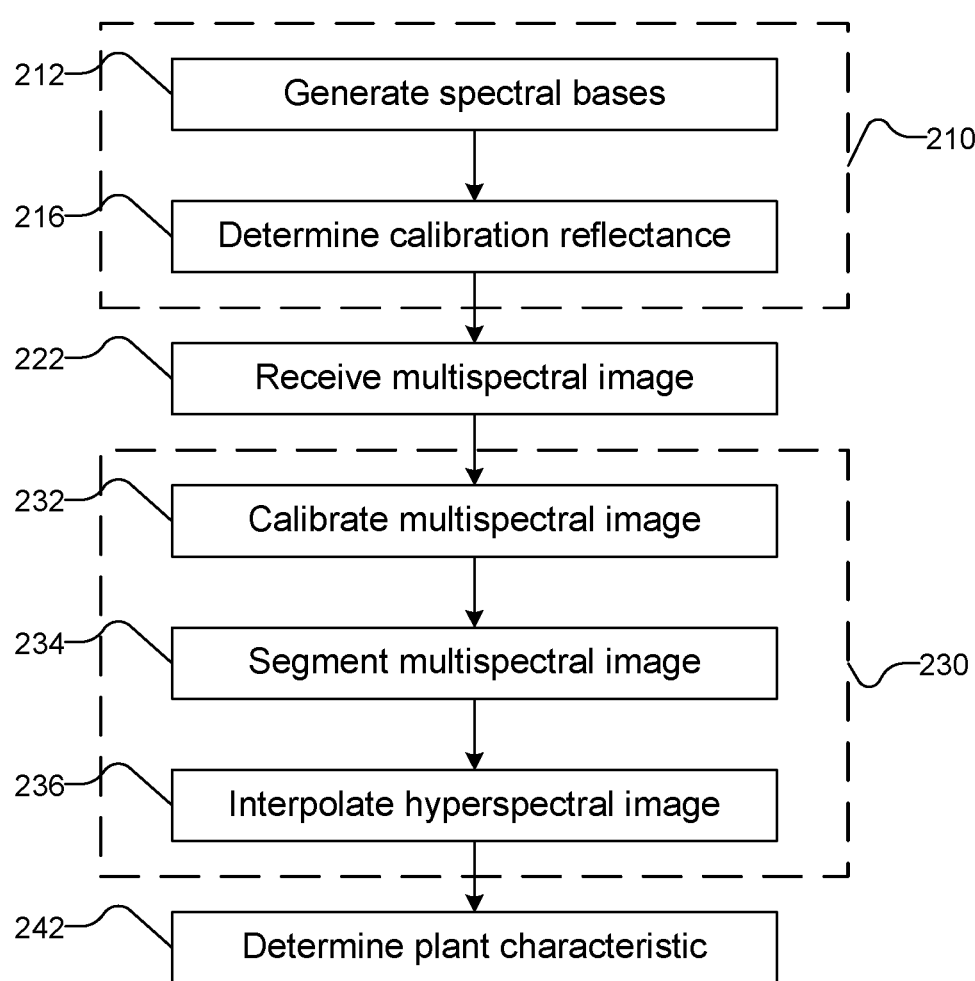

A Method for Generating Hyperspectral Images of Plants from Multispectral Images FIG. 2 is a flowchart illustrating an example method 200 for generating hyperspectral images based on multispectral images. Method 200 is performed by a computing system, as described elsewhere herein (e.g. with reference to FIG. 6). Method 200 may, optionally, comprise calibration acts 210 (e.g. based on one or more reference and/or calibration images). Method 200 acquires a multispectral image at act 222, generates a hyperspectral image therefrom at acts 230, and determines one or more plant characteristics based on the hyperspectral image at act 242. Each of these acts is discussed in greater detail below.

Method 200 involves interpolating spectral information based on a plurality of spectral bases. Such spectral bases may be predetermined, generated as part of method 200, and/or otherwise obtained. In some embodiments, including the illustrated example of FIG. 1, method 200 generates a plurality of spectral bases based on one or more reference images at act 212. Reference images may comprise hyperspectral images, which may have no spatial dimension (e.g. hyperspectral readings produced by a spectrometer), one or two spatial dimensions, and/or any other suitable number of spatial dimensions.

Act 212 may comprise determining characteristic spectra of the one or more reference images and describing the characteristic spectra as spectral bases comprising a set of basis vectors. For instance, given a set of p reference images, each image comprising spectral intensity $$s(\lambda) = [s(\lambda_1), s(\lambda_2), \ldots, s(\lambda_n)]^T$$

where $s(\lambda_i)$ is the spectral intensity for the $i^{th}$ wavelength (or channel) $\lambda_i$, the computing system may generate a correlation matrix $$R = \sum_{i=1}^{p} s_i(\lambda) s_i(\lambda)^T$$

and determine therefrom the eigenvectors to $\{\sigma_j\}$ of R. Each eigenvector is a potential basis vector; the computing system may generate the spectral bases by selecting a plurality of the eigenvectors (which may comprise some or all of the eigenvectors $\sigma_j$). The computing system may optionally transform the basis vectors, e.g. by normalizing them. Further details on generation of spectral bases is provided by Parkkinen et al., *Characteristic spectra of munsell colors*, Journal of the Optical Society of America A 6 (1989) 318-322, which is incorporated by reference.

In some embodiments, the computing system generates (and/or otherwise receives) one or more spectral bases based on one or more reference images representing at least a portion of a plant. For example, the one or more reference images may comprise one or more hyperspectral images of healthy plants. In at least one embodiment, the one or more reference images comprise a plurality of hyperspectral images of non-plant matter such as Munsell chips (substantially as described by Parkkinen et al., referenced above) and further comprise hyperspectral images of healthy plants and/or portions thereof, such as healthy leaves. Such hyperspectral reference images of healthy plants may comprise measurements of plants' reflectance intensity in infrared spectral wavelengths, such as in near-IR spectral wavelengths (e.g. approx. 700 nm to 800 nm). In some embodiments, the computing system generates a number of eigenvalues as described above based on the reference images and selects from them a number of spectral bases. In at least one embodiment, the computing system selects four spectral bases. Experimentation with such example embodiments has demonstrated that the accuracy of hyperspectral interpolation of method 200 can be improved by the inclusion of such plant spectral information in the spectral bases, in at least some circumstances.

Optionally, at act 216 the computing system determines one or more intensities of reflectance of a calibration image (called calibration reflectance values herein), e.g. for optional use in calibrating images at act 232. The calibration image may comprise, for example, a multispectral image (e.g. having the same or similar multispectral channels to those received at act 222, described elsewhere herein) representing a calibration subject which is substantially non-reflective in one or more of the calibration image's multispectral channels. In some embodiments the calibration subject comprises a black patch positioned in the field of view of a multispectral imaging apparatus, the black patch being substantially non-reflective in visible and near-IR spectra. The computing system may measure an intensity of reflectance at one or more spatial locations (e.g. pixels of the multispectral image) representing the calibration subject for at least one of the spectral channels of the calibration image and determine from these a calibration reflectance (e.g. by using the value of the spectral intensity as provided by the multispectral image, by averaging the intensities in a channel at multiple spatial locations, and/or in any other suitable way). For example, in at least one embodiment, the computing system calculates an average calibration reflectance intensity $c(\lambda_i)$ for a plurality of pixels representing a substantially non-reflective black patch in each channel $\lambda_i$.

At act 222, the computing system receives a multispectral image representing at least a portion of a plant. The multispectral image comprises m spectral channels (called multispectral channels herein for convenience), at least one of which comprises an infrared wavelength. For instance, the multispectral image may comprise at least one channel comprising a wavelength in the near-IR spectrum, e.g. in approx. 700 nm to 800 nm and/or 700 nm to 1000 nm. The multispectral image may comprise at least one channel in the green spectrum, e.g. in approx. 525 nm to 575 nm. The multispectral image may comprise one or more channels with wavelengths shorter than the green spectrum (e.g. in the 400 nm to 500 nm range), between the green and infrared spectra (e.g. in the 600 nm to 700 nm range), and/or longer than the near-IR spectrum (e.g. longer than 1000 nm). In some embodiments, the multispectral image comprises at least four spectral channels, to aid in interpolation.

In some example embodiments, the multispectral image comprises seven channels with center wavelengths of 450 nm, 500 nm, 550 nm, 600 nm, 650 nm, 700 nm, and 750 nm, respectively. In one example embodiment, each of these seven channels has a FWHM bandwidth of 50 nm. In another example embodiment, each such channel has a FWHM bandwidth of nm. These example embodiments further comprise an eighth channel covering the visible spectrum (roughly 400 nm to 700 nm).

In some embodiments, act 222 comprises generating the multispectral image from frames generated by an imaging device. For example (e.g. as described in greater detail with reference to FIG. 6), the computing system may receive a plurality of frames captured by an imaging device, each frame captured through one of a plurality of optical filters (which may, e.g., revolve through a field of view of the imaging device as it captures frames). The imaging device may comprise, for example, an RGB camera with near-IR sensitivity (e.g. in the blue channel) generating 3-channel RGB frames, a monochrome CCD sensor generating single-channel frames, and/or any other suitable imaging device. The computing system may combine the plurality of frames into a multispectral image, e.g. with each multispectral channel corresponding to an optical filter. In at least some embodiments, the computing system receives frames as raw sensor data—e.g. without automatic white balancing, adjusted exposure, or other common adjustments (often intended to improve the appearance of images to the human eye), which modify spectral characteristics and can interfere with certain applications, such as those which require accurate readings of relative reflectance.

In some embodiments the imaging device generates multichannel frames (e.g. as with an RGB camera). In such embodiments, act 222 may comprise combining the multiple channels of a frame into a single channel (and/or a reduced number of channels) and/or combining frames' channels non-destructively (e.g. via concatenation). For example, act 222 may comprise generating a multispectral image having a channel for each optical filter through which the imaging device generates an image by summing the intensities of each channel for a given frame to form one intensity for the multispectral channel corresponding to the optical filter through which the frame was captured. In some embodiments, summing the intensities of a frame's channels may comprise performing a weighted sum and/or integration of the intensities of the channels, weighted according to the relative sensitivities of the imaging device's sensors for each of the imaging device's channels.

Optionally, at act 232, the computing system calibrates the multispectral image. Calibration may comprise, for example, correcting one or more channels of the multispectral image based on the calibration reflectance values generated at act 216 (e.g. based on a black patch). For instance, the computing system may subtract, from each of one or more channels (and optionally all channels) of the multispectral image, the calibration reflectance corresponding to that channel. This can reduce the effect of optical imperfections in the imaging system, unexpected/leaky illumination in the environment, and/or other miscalibrations. Act 232 may alternatively or additionally comprise any suitable calibration technique, such as adding a highly reflective calibration subject (e.g. a diffuse white board), such as is described in greater detail by Han et al. (2011) *Fast Spectral Reflectance Recovery Using DLP Projector*, Computer Vision—ACCV 2010. Lecture Notes in Computer Science, vol 6492. doi:10.1007/978-3-642-19315-6_25, which is incorporated herein by reference.

Act 232 may occur as part of act 222, act 236, and/or separately (e.g. afterwards). For example, suppose the calibration image comprises a plurality of RGB frames, e.g. in an exemplary embodiment where the imaging device comprises an RGB camera as described above with reference to act 222. Suppose also that the calibration image represents a black patch which is substantially non-reflective in each of the channels of the calibration image (and/or the multispectral image). If the computing system generated at act 216 a calibration reflectance of [16,0,0] for an RGB frame of the calibration image captured through a 650 nm optical filter (e.g. with 50 nm FWHM bandwidth), thereby indicating an intensity of 16 in the "red" channel, the computing system may subtract that calibration reflectance from an RGB frame received at act 222 which is also associated with the 650 nm optical filter. For instance, if that RGB frame has intensities [32, 105, 12], the computing system may correct those intensities based on the calibration reflectance to determine a corrected reflectance of [16, 105, 12]. The computing system may proceed to combine the corrected RGB frame with other frames as described in act 222. Alternatively, or in addition, the computing system may combine frames for the calibration image to generate a single, scalar calibration reflectance for a given wavelength and may correct the multispectral image of act 222 based on such scalar calibration reflectance. In some embodiments, the computing system alternatively or additionally corrects reflectance values of the hyperspectral image of act 236 based on the calibration reflectance values of act 216.

Optionally, at act 234 the computing system segments the multispectral image to classify regions of the multispectral image as representing plant or non-plant (e.g. background) objects. Any suitable segmenting method may be used; for example, the computing system may classify plants as foreground and non-plants as background based on Otsu thresholding. In some embodiments, the computing system performs segmentation based on one frame of the multispectral image (e.g. a frame captured through a shortpass filter covering some or all of the visible spectrum, and/or a frame comprising a conventional RGB image to facilitate segmentation by available segmentation models) and may apply that segmentation mask to all frames of the multispectral image. Subsequent acts based on the hyperspectral image, such as interpolation at act 236, may be limited to portions of the multispectral image classified as plant. This may, for example, reduce the computational resources required to generate the hyperspectral image at act 236 and/or generate determinations about plant characteristics at act 242. In some embodiments, the computing system alternatively or additionally performs segmentation on the hyperspectral image generated from the multispectral image.

In some embodiments, the computing system applies morphological adjustments to reduce the likelihood of including non-plant objects in plant-labelled regions, such as by applying binary closing and/or binary erosion. Although such adjustments are not always desirable, for at least some applications of the present techniques it can be desirable to make such adjustments to reduce the likelihood that non-plant objects will be included in regions classified as plant. For example, where the computing system will use the resulting hyperspectral image to assess plant health based on the spectral characteristics of the plant, such adjustments may be desirable in suitable circumstances.

At act 236, the computing system generates a hyperspectral image based on the multispectral image and a plurality of spectral bases (e.g. the spectral bases generated at act 212 and/or otherwise obtained). The hyperspectral image at least partially represents the (at least a portion of a) plant represented in the multispectral image. The computing system generates the hyperspectral image to comprise a greater number n of spectral channels (called hyperspectral channels herein for convenience) than the number m of multispectral channels of the multispectral image. Such generating may comprise interpolating at least one reflectance value for a spatial location (e.g. a pixel) of the hyperspectral image and for a given wavelength (e.g. corresponding to one of the hyperspectral channels) outside of the m multispectral channels.

Such interpolation may be based on the m multispectral channels.

For example, supposing the imaging device generating the multispectral image has a linear intensity response and generates frames having one or more spectral channels, the intensity $I_{m,n}$ of a spatial location (e.g. a pixel) in the hyperspectral image may be determined based on:

$$I_{m,n} = \int s(\lambda) c_m(\lambda) l_n(\lambda) d\lambda$$

where $\lambda$ is the wavelength (and/or channel), $s(\lambda)$ is the spectral reflectance at the spatial location for $\lambda$, $c_m(\lambda)$ is the spectral response function of the imaging device at the $m^{th}$ colour channel, and $l_n(\lambda)$ is the spectrum of the $n^{th}$ frame.

Spectral reflectance $s(\lambda)$ can be recovered from such a linear model based on the spectral bases. In particular, the spectral reflectance for a given spatial location may be determined based on:

$$s(\lambda) = \sum_{j=1}^{d} \alpha_j b_j(\lambda)$$

where $b_j(\lambda)$ is the $j^{th}$ spectral basis and $\alpha_j$ is a corresponding coefficient which may be estimated based on any suitable technique. An example technique for estimating $\alpha_j$ is provided, for example, by Han et al. (2011) *Fast Spectral Reflectance Recovery Using DLP Projector*, Computer Vision—ACCV 2010. Lecture Notes in Computer Science, vol 6492. doi:10.1007/978-3-642-19315-6_25, which is incorporated herein by reference.

In some embodiments, act 236 comprises generating (e.g. interpolating) spectral reflectance values at spatial locations labelled as plant at act 234, without necessarily doing so at other spatial locations.

At act 242, the computing system generating a determination for the (at least the portion of a) plant based on the hyperspectral image. For example, the computing system may predict a measure of plant health based on the hyperspectral image, e.g. as described in greater detail with reference to method 200.

A System for Hyperspectral Imaging of Plants

Figure 3:
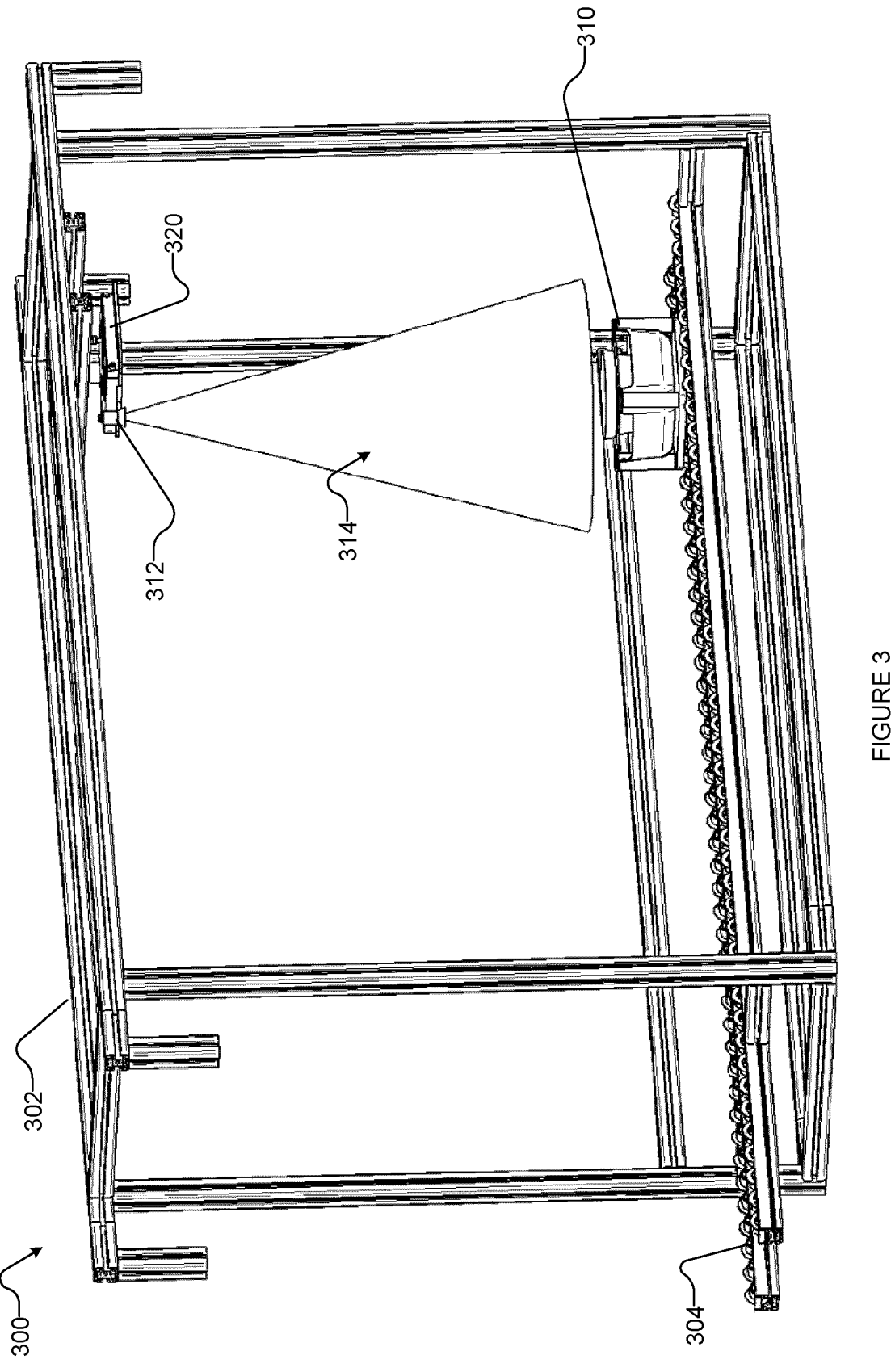
FIG. 3 is a perspective view schematic diagram illustrating an example apparatus for imaging plants, which images may be used by the methods of FIGS. 1 and 2.
Figure 4:
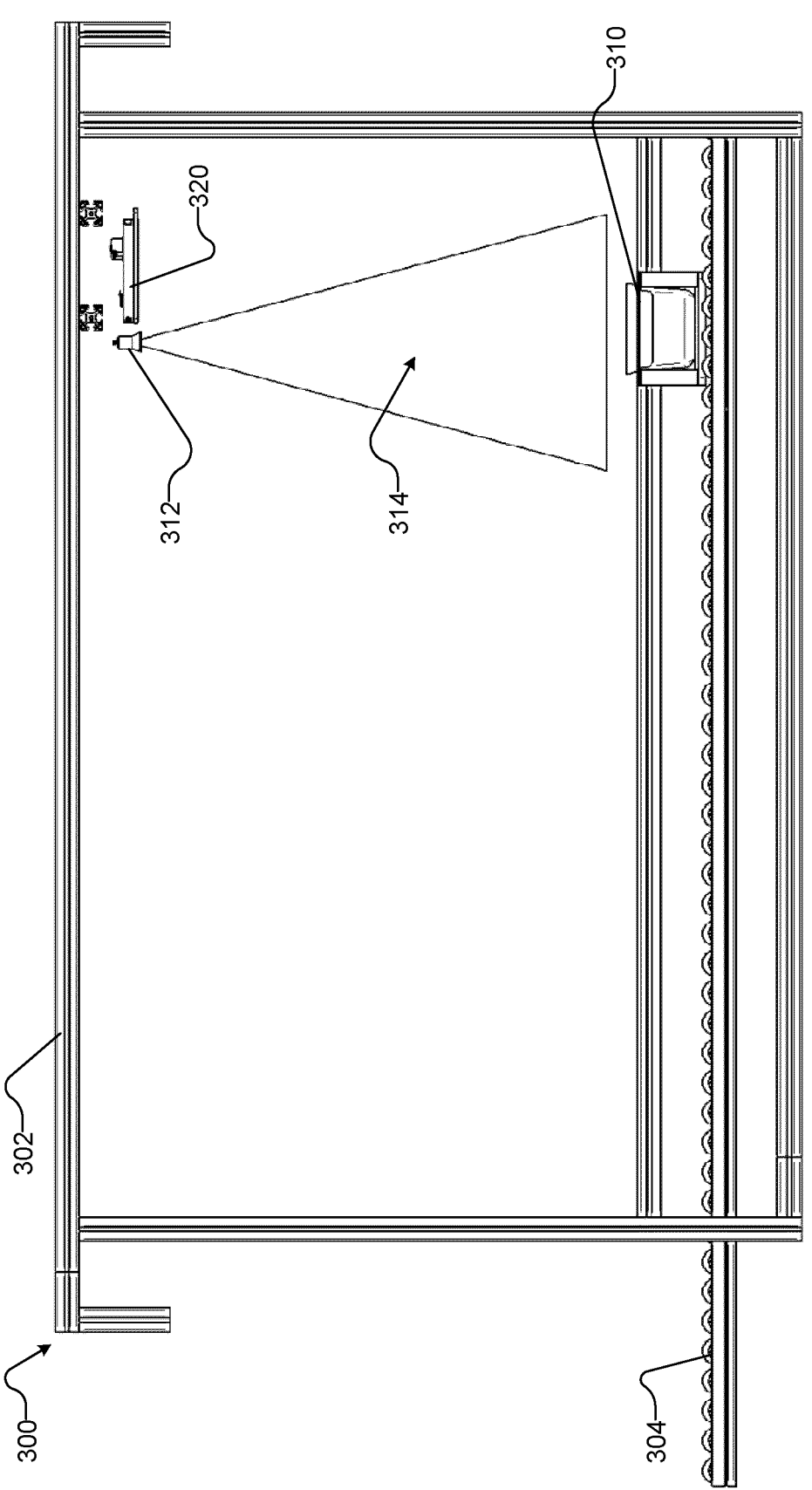
FIG. 4 is a side elevation view schematic diagram of the example apparatus of FIG. 3.
Figure 5:
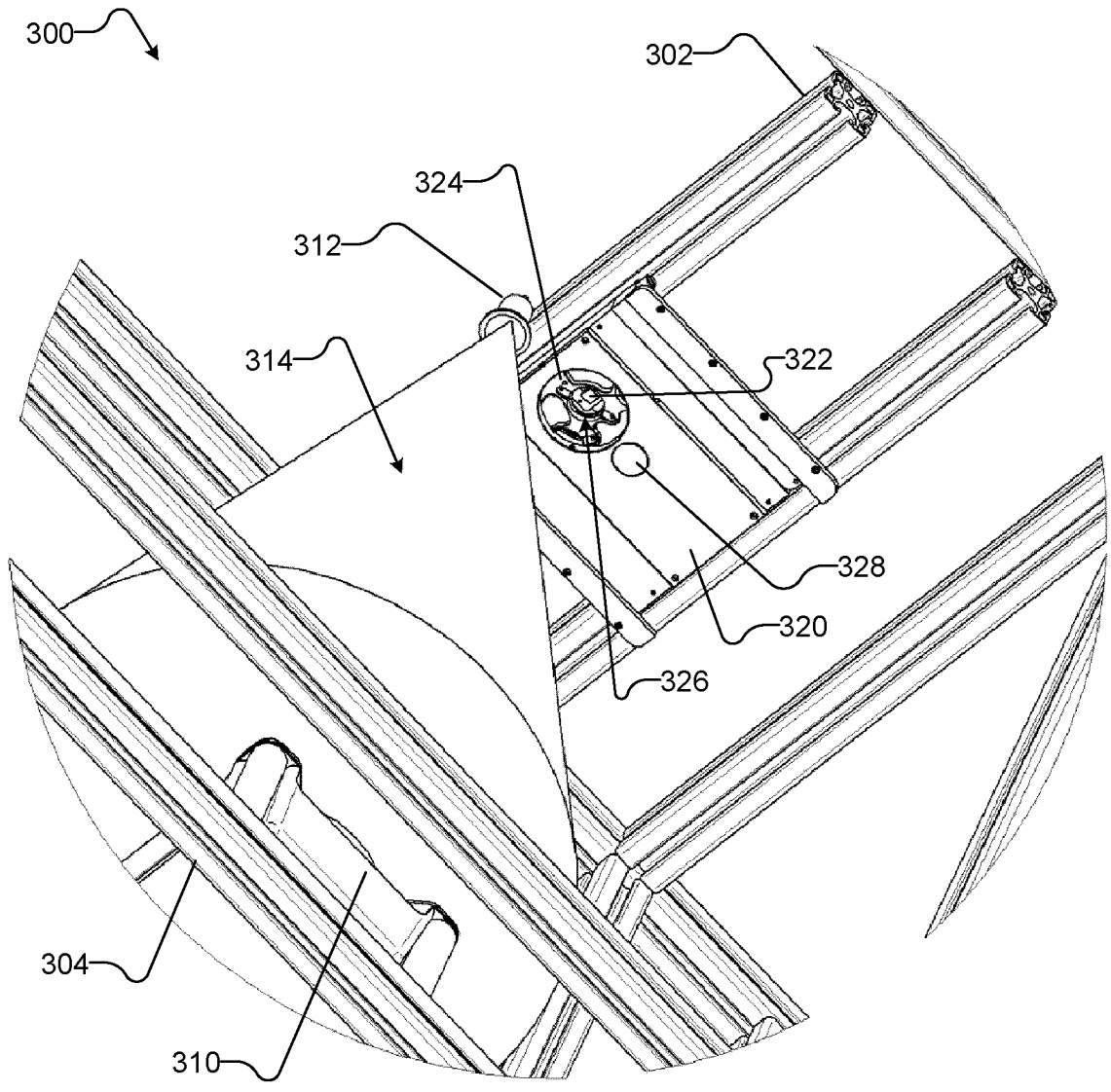
FIG. 5 is a detail view schematic diagram of a portion of the example apparatus of FIG. 3 shown in a perspective orientation generally from below, illustrating generally an example planter, illumination source, and camera.

FIGS. 3, 4, and 5 are schematic diagrams of an example apparatus 300 for imaging plants. Such images may be multispectral and/or hyperspectral and may optionally be used by methods 100 and/or 200. FIG. 3 provides a perspective view for context, FIG. 4 provides a side elevation view, and FIG. 5 provides an enlarged detail view shown in a perspective orientation generally from below to show certain elements of a camera and associated elements. FIGS. 3, 4, and 5 are discussed together.

Apparatus 300 comprising an illumination source 312 and an imaging device 320. Illumination source 312 illuminates a region 314 which substantially aligns with a field of view of imaging device 320. In the example embodiment of FIGS. 3-5, apparatus 300 comprises a frame 302 for supporting illumination source 312 and imaging device 320. Apparatus 300 may further comprise a conveyor 304 (e.g. supported by frame 302) for conveying plants and/or other imaging subjects through region 314. Plants may, for example, be supported by a planter 310 conveyed by conveyor 304.

In some embodiments, apparatus 302 comprises a shroud (not shown) for blocking and/or otherwise reducing external illumination in region 314. For example, the shroud may comprise walls and/or other substantially opaque surfaces around (and optionally supported by) frame 302. In some embodiments, apparatus 300 comprises a movable barrier along conveyor 304 (and optionally two movable barriers on opposing sides of region 314) which are openable to admit a plant and/or planter 310 to region 314 for imaging and/or to allow the plant and/or planter 310 to exit region 314 subsequent to imaging. Such movable barriers may be opaque and may be controlled by apparatus 300 (e.g. via a controller, not shown) to shut, thereby blocking and/or otherwise reducing external illumination in region 314 during imaging by imaging device 320.

An exemplary embodiment of imaging device 320 is shown in greater detail in FIG. 5. Imaging device 320 comprises an imaging sensor 322. For example, imaging device 320 may comprise an RGB camera with near-IR sensitivity. For instance, in an exemplary embodiment, imaging device 320 comprises a Sony™ IMX219 module (comprising an imaging sensor 320) for a Raspberry Pi™ controller (not shown). Other elements of apparatus 300, such as illumination source 312, conveyor 304, movable barriers, may optionally be controlled by such controller and/or by one or more other controllers (e.g. such as by a computing system, as described with reference to FIG. 6).

Imaging device 320 may further comprise one or more optical filters 326. In some embodiments, imaging device 320 comprises a plurality of optical filters 326. For example, imaging device 320 may comprise a filter wheel 324 comprising a plurality of optical filters 326. Imaging device 320 may drive filter wheel 324 (e.g. via a rotor 328) to revolve optical filters 326 through a field of view of imaging sensor 322 to allow imaging sensor 322 to capture images through such optical filters 326. Rotor 328 may drive filter wheel 324 continuously and/or rotor 328 may drive filter wheel 324 intermittently, e.g. by pausing during an exposure of imaging sensor 322 through a given optical filter 326.

In at least the depicted exemplary embodiment, filter wheel 324 comprises eight optical filters: seven bandpass filters with center wavelengths of 450 nm, 500 nm, 550 nm, 600 nm, 650 nm, 700 nm, and 750 nm, respectively, with each a FWHM bandwidth of 25 nm, and one shortpass filter blocking wavelengths longer than approx. 700 nm. Such a shortpass filter may, in suitable embodiments (e.g. those comprising a near-IR sensitive RGB and/or monochrome camera) facilitating the capture of conventional, visible-spectrum-only images by imaging sensor 322. Such images may be used for segmentation, display, and/or any other purpose.

Example System Implementation

Figure 6:
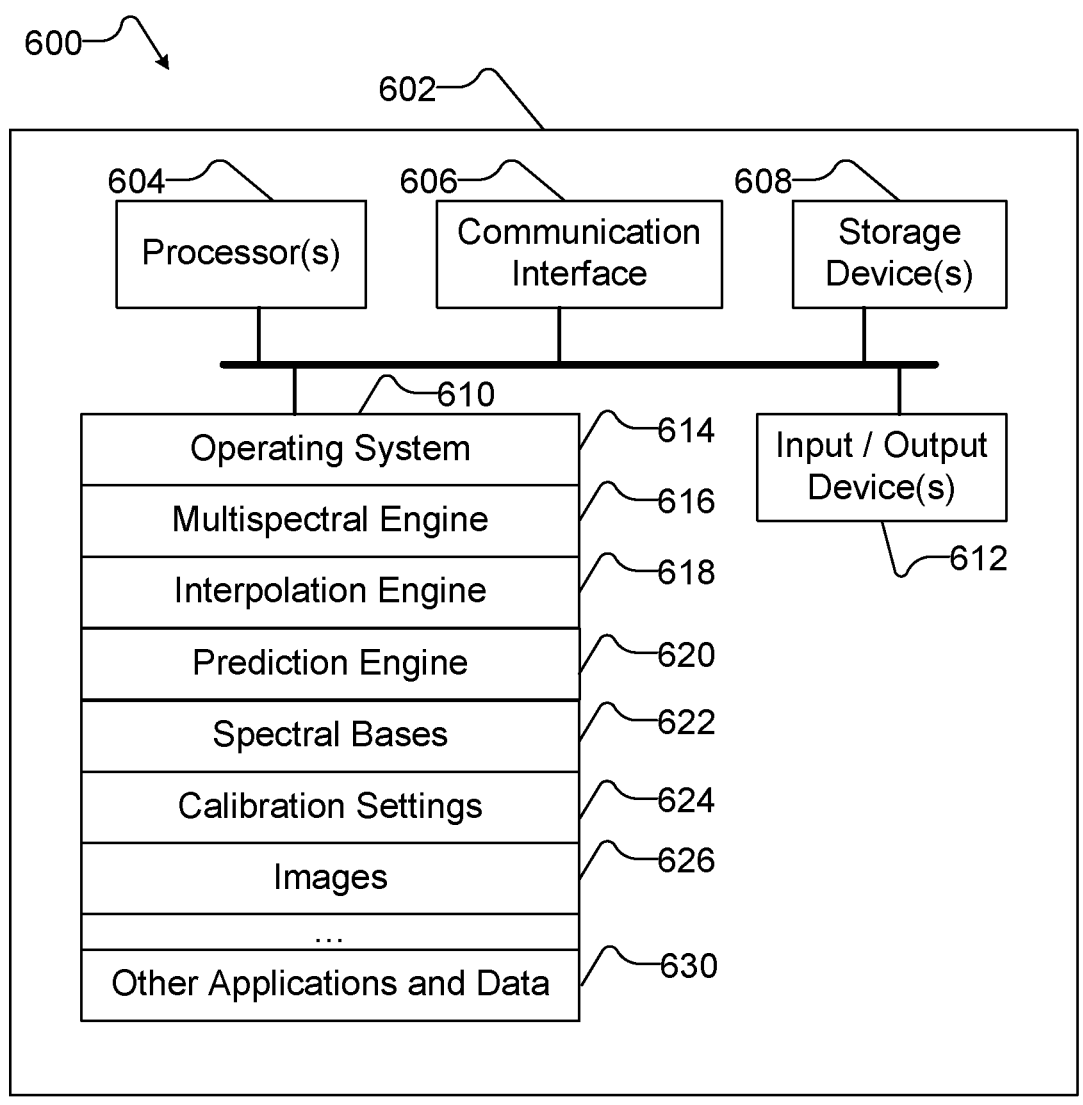
FIG. 6 shows a first exemplary operating environment that includes at least one computing system for performing methods described herein, such as the methods of FIGS. 1 and 2.

FIG. 6 illustrates a first exemplary operating environment 600 that includes at least one computing system 602 for performing methods described herein. System 602 may be any suitable type of electronic device, such as, without limitation, a mobile device, a personal digital assistant, a mobile computing device, a smart phone, a cellular telephone, a handheld computer, a server, a server array or server farm, a web server, a network server, a blade server, an Internet server, a work station, a mini-computer, a mainframe computer, a supercomputer, a network appliance, a web appliance, a distributed computing system, multiprocessor systems, or combination thereof. System 602 may be configured in a network environment, a distributed environment, a multi-processor environment, and/or a stand-alone computing device having access to remote or local storage devices.

A computing system 602 may include one or more processors 604, a communication interface 606, one or more storage devices 608, one or more input and output devices 612, and a memory 610. A processor 604 may be any commercially available or customized processor and may include dual microprocessors and multi-processor architectures. The communication interface 606 facilitates wired or wireless communications between the computing system 602 and other devices. A storage device 608 may be a computer-readable medium that does not contain propagating signals, such as modulated data signals transmitted through a carrier wave. Examples of a storage device 608 include without limitation RAM, ROM, EEPROM, flash memory or other memory technology, CD-ROM, digital versatile disks (DVD), or other optical storage, magnetic cassettes, magnetic tape, magnetic disk storage. In at least some embodiments such embodiments of storage device 608 do not contain propagating signals, such as modulated data signals transmitted through a carrier wave. There may be multiple storage devices 608 in the computing system 602. The input/output devices 612 may include a keyboard, mouse, pen, voice input device, touch input device, display, speakers, printers, etc., and any combination thereof.

The memory 610 may be any non-transitory computer-readable storage media that may store executable procedures, applications, and data. The computer-readable storage media does not pertain to propagated signals, such as modulated data signals transmitted through a carrier wave. It may be any type of non-transitory memory device (e.g., random access memory, read-only memory, etc.), magnetic storage, volatile storage, non-volatile storage, optical storage, DVD, CD, floppy disk drive, etc. that does not pertain to propagated signals, such as modulated data signals transmitted through a carrier wave. The memory 610 may also include one or more external storage devices or remotely located storage devices that do not pertain to propagated signals, such as modulated data signals transmitted through a carrier wave.

The memory 610 may contain instructions, components, and data. A component is a software program that performs a specific function and is otherwise known as a module, program, engine, and/or application. The memory 610 may include an operating system 614, a multispectral engine 616, an interpolation engine 618 (e.g. if a given embodiment generates hyperspectral images from multispectral images as described elsewhere herein), a prediction engine 620, spectral bases 622, calibration settings 624, one or more images 626 (e.g. multispectral images and/or hyperspectral images, which may comprise reference images), and other applications and data 630. Depending on the embodiment, some such elements may be wholly or partially omitted. For example, an embodiment intended for prediction based on received multispectral and/or hyperspectral images may exclude interpolation engine 618. As another example, memory 610 may include no images 626 prior to performing a method described herein and may receive such images via an input device 612 and/or from a storage device 608 and/or generate such images as described elsewhere herein.

Example Application

Figure 7:
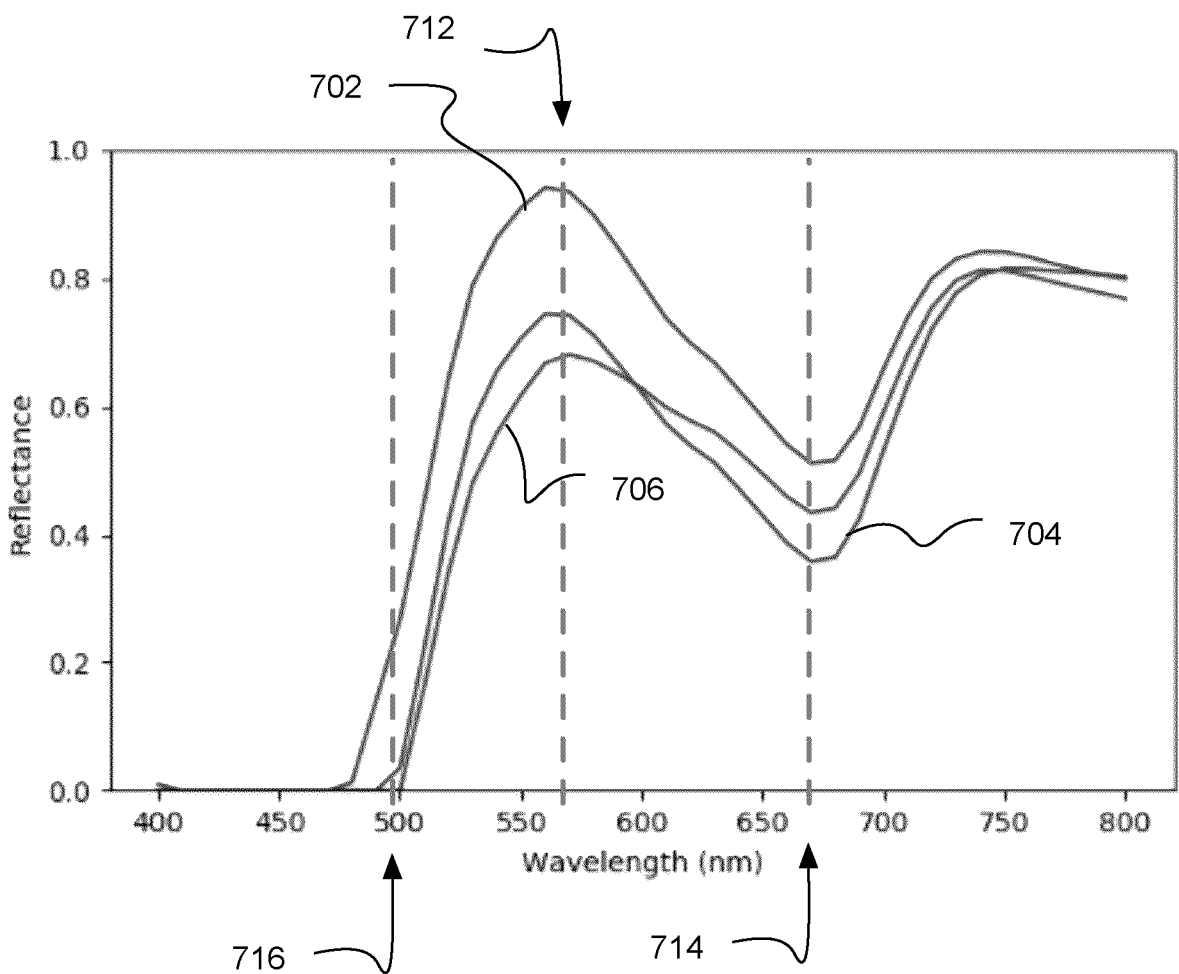
FIG. 7 shows an example chart depicting measured reflectances of locations on wheat leaves under various environmental conditions and levels of disease pressure.

In at least one example embodiment, the reference derivative comprises a measure of slope across a first wavelength and a second wavelength selected for a given plant and/or plant disease. FIG. 7 shows an example chart depicting actual measured reflectances 702, 704, 706 of locations on wheat leaves under various environmental conditions and levels of disease pressure. Measured reflectances 702 correspond to a location on a first healthy wheat leaf. Measured reflectances 704 correspond to a second healthy wheat leaf. Measured reflectances 706 correspond to a location on an unhealthy wheat leaf. The unhealthy wheat leaf in the example of FIG. 7 is in the early stages of infection with wheat rust.

In some embodiments, the plant and/or portion thereof exhibit a maximal reflectance at approximately a wavelength 712, a minimal reflectance at approximately a wavelength 714, and (optionally) a baseline reflectance at approximately a wavelength 716 outside of the spectral region between wavelengths 712 and 714. Here, "maximal" and "minimal" are used in a local sense, i.e. referring to a local maximum and local minimum. In some embodiments, wavelengths 712 and 714 correspond to adjacent minima/maxima. For example, as shown in FIG. 7, both healthy and unhealthy wheat leaves are observed to provide a maximal reflectance at wavelengths of approximately 570 nm (wavelength 712), a minimal reflectance at wavelengths of approximately 670 nm (wavelength 714), and a baseline reflectance at wavelengths of approximately 500 nm (wavelength 716).

In at least some embodiments, wavelength 716 is selected such that the baseline reflectance is less than the reflectances of wavelengths 712 and/or 714. For example, wavelength 716 may be selected such that the baseline reflectance is less than the reflectances of wavelengths 712 and 714 by at least a threshold (such as 50% of the minimal reflectance). Another example, wavelength 716 may be selected to capture dispersion in baseline reflectances between images of healthy plants and/or portions thereof, e.g. by selecting wavelength 716 such that the baseline reflectance is no greater than a threshold (e.g. a threshold near 0) for a first reference image of a healthy plant and/or portion thereof in a first set of environmental and/or optical conditions and such that the baseline reflectance is greater than a threshold (which may be the same or a different threshold) for a second reference image of a healthy plant and/or portion thereof in a second set of environmental and/or optical conditions. As yet another example, wavelength 716 may be selected to capture distinctions in absolute reflectance between healthy and unhealthy plants even where differences in derivatives may not be readily discerible, e.g. by selecting wavelength 716 such that the baseline reflectance is no greater than a threshold (e.g. a threshold near 0) for a first reference image of an unhealthy plant and/or portion thereof and such that the baseline reflectance is greater than a threshold (which may be the same or a different threshold) for a second reference image of a healthy plant and/or portion thereof, e.g. as shown in FIG. 7. Such baseline reflectances may not be reliable sole indicators of health (for instance, in the example of FIG. 7 both healthy reflectance 704 and unhealthy reflectance 706 are near-zero around wavelength 716), but in embodiments a high baseline reflectance may be associated with plant health.

In some embodiments, a measure of plant health may be provided by determining a derivative for at least a portion of spectrum between the maximal and minimal wavelengths. In some embodiments, the derivative may be approximated based on a difference between the maximal and minimal reflectances (i.e. reflectances at wavelengths 712 and 714), e.g. based on $R_{max}-R_{min}>t$, where $R_{max}$ and $R_{min}$ are the maximal and minimal reflectances (respectively) for a given spectral measurement of the plant and/or portion thereof and t is a suitable threshold such that measures in excess of t are determined to be healthy and measures of less than t are determined to be unhealthy. In some embodiments, the measure of plant health comprises a measure of plant disease. A measure of plant disease may be based on an inverse of a foregoing measure, such as $R_{max}-R_{min}<t$. Alternatively, or in addition, a continuous (or otherwise non-binary) measure of plant health may be determined based on $R_{max}-R_{min}$.

In some embodiments, $R_{max}$ and $R_{min}$ are reflectances at wavelengths between wavelengths 712 and 714. For instance, in an example embodiment where wavelength 712 is approximately 570 nm and wavelength 714 is approximately 670 nm, $R_{max}$ may correspond to reflectance at a wavelength of 600 nm and $R_{min}$ may correspond to reflectance at a wavelength of 650 nm. That is, any wavelength in the spectral region between approximately wavelengths 712 and 714 may optionally be used to estimate the derivative over the spectral region between approximately wavelengths 712 and 714.

In some embodiments, the measure of plant health is based on a normalized derivative; normalization may be based on a measure of total reflectance across at least the portion of spectrum between the maximal and minimal wavelengths. Such normalization may assist in limiting noise introduced by variations in illumination, angle of reflectance, and/or other factors. For example, such total reflectance may be approximated based on a sum of reflectances between the maximal and minimal reflectances, e.g. based on $R_{max}+R_{min}$. For instance, the measure of plant health may be based on:

$$\frac{R_{max} - R_{min}}{R_{max} + R_{min}} > t$$

In some embodiments, the measure of plant health is based on the baseline reflectance (denoted $R_{base}$), for instance by adding the baseline reflectance to a measure described elsewhere herein. The baseline reflectance may contribute a (potentially non-determinative) signal of health as described above. For instance, the measure of plant health may be based on:

$$\frac{R_{max} - R_{min}}{R_{max} + R_{min}} + R_{base} > t$$

In some embodiments, the measure of plant health is determined based on a multispectral image of a plant and/or a portion thereof on a per-pixel basis. For example, each pixel associated with (e.g. labelled as) a plant and/or a portion thereof may have a per-pixel plant health measure associated with it, and an aggregate plant health measure may be determined for the plant and/or portion thereof based on an aggregate (e.g. an average) of the per-pixel plant health measures. For instance, given a collection p of n pixels associated with a plant and/or portion thereof, an aggregate plant health measure m may be based on an average of per-pixel plant health measures over p, e.g. based on:

$$m = \frac{\Sigma_p \frac{R_{max} - R_{min}}{R_{max} + R_{min}} + R_{base}}{n}$$

For example, returning to the wheat leaf/wheat rust example of FIG. 7, a plant health measure m for a plant and/or portion thereof represented in a multispectral image where pixels p have been associated with the plant and/or portion thereof may be determined based on:

$$m = \frac{\Sigma_p \frac{R570 - R670}{R570 + R670} + R500}{n}$$

where R570 is the measured reflectance for a pixel p at a wavelength of approximately 570 nm, R670 is the measured reflectance for a pixel p at a wavelength of approximately 670 nm, and R500 is the measured reflectance for a pixel p at a wavelength of approximately 500 nm.

Figure 8:
FIG. 8 shows example distributions of results of an exemplary foregoing metric applied to a dataset of multispectral images of wheat leaves.
Figure 8:
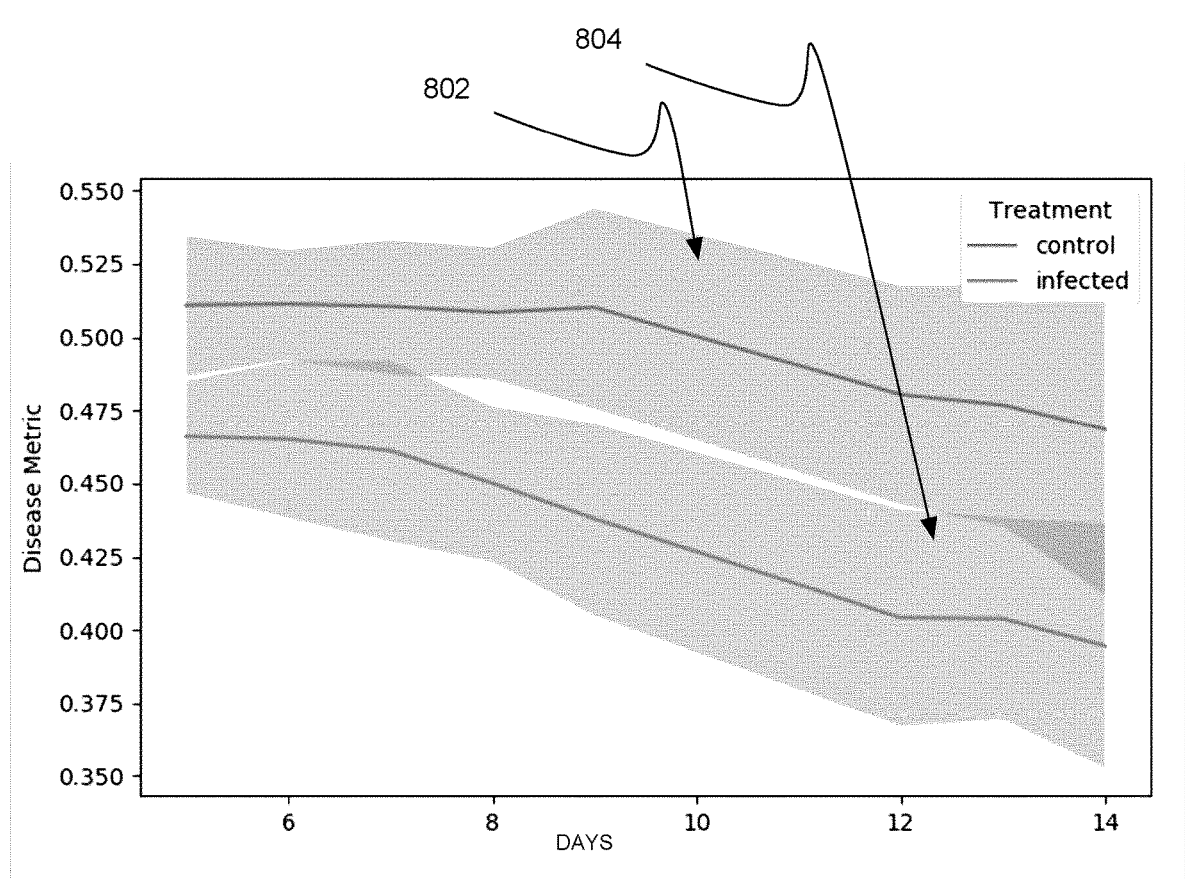

Example distributions of results of the foregoing metric m applied to a dataset of multispectral images of wheat leaves are shown in the chart 800 of FIG. 8. Distribution 802 of plant health measure values for control plants (i.e. those not deliberately infected with wheat rust on the first day of trials) shows good separation from distribution 804 of plant health measure values for infected plants (i.e. those deliberately infected with wheat rust on the first day of trials) even as early as five days post-infection. Ordinary visual inspection of wheat leaves might not identify disease until much later (e.g. 14 days). The foregoing metric may thus potentially provide early detection of disease in wheat in suitable circumstances.

In some embodiments, the derivatives of method 100 comprise measures as described herein with reference to FIGS. 7 and/or 8. For example, act 102 may comprise generating a reference healthy reflectance (for at least the selected wavelengths, e.g. wavelengths 712, 714, and/or 716) as described herein based on multispectral images of healthy plants. Act 104 may comprise generating a reference unhealthy reflectance (for at least the selected wavelengths, e.g. wavelengths 712, 714, and/or 716) as described herein based on multispectral images of unhealthy plants. Act 104 may comprise determining reference derivative(s) based on the reference reflectance(s) of act 102, e.g. by determining a plant health measure for one or more plants and/or portions thereof represented in the multispectral images as described above. Act 108 may comprise determining a derivative by determining a plant health measure (e.g. as described above) for one or more plants and/or portions thereof represented in the multispectral images received at act 106. Act 110 may comprise determining a loss metric between the derivative of act 108 to the derivative(s) of act 104. The loss metric may be determined in any suitable way, e.g. as described elsewhere herein with reference to act 110. In some embodiments, act 110 comprises determining a loss metric of the target derivative relative to each of the healthy and unhealthy reference reflectances' derivatives; act 112 may comprise generating a prediction based on a determination of which of the healthy and unhealthy reflectances is associated with a lower loss metric value.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method for spectral characterization of plants, the method performed by a processor and comprising:
   receiving an input multispectral image comprising a number m of spectral channels, at least one spectral channel comprising an infrared wavelength, the multispectral image representing at least one portion of at least one plant;
   generating a multispectral image comprising a number n of multispectral channels based on the input multispectral image and a plurality of spectral bases, the number n of multispectral channels greater than the number m of input multispectral channels;
   generating a determination for the at least one portion of the at least one plant based on the multispectral image based on a derivative of a plurality of reflectance values of the multispectral image with respect to wavelength.

2. The method according to claim 1 wherein the determination comprises a prediction of plant health and generating the determination comprises determining the prediction of plant health based on the derivative of the plurality of reflectance values and a plurality of reference reflectance values.

3. The method according to claim 2 further comprising generating the plurality of reference reflectance values based on a reference multispectral image representing at least a healthy portion of a reference plant, optionally wherein generating the plurality of reference reflectance values comprises determining an average of reflectance values for a plurality of spatial locations of the at least the healthy portion of the reference plant for each of a plurality of spectral channels of the reference multispectral image.

4. The method according to claim 2 wherein determining the prediction of plant health comprises determining a difference between the derivative of the plurality of reflectance values and a derivative of the plurality of reference reflectance values with respect to wavelength.

5. The method according to claim 4 wherein determining the difference comprises determining a regression loss metric based on the derivative of the plurality of reflectance values and a derivative of the plurality of reference reflectance values, wherein the regression loss optionally comprises at least one of: a mean square error, a mean absolute error, a Huber loss, a log-cosh loss, and a quantile loss.

6. The method according to claim 2 wherein the plurality of reference reflectance values comprise a first plurality of reference reflectance values corresponding to at least a first portion of at least a first plant and a second plurality of reference reflectance values corresponding to at least a second portion of at least a second plant, the first and second portions differing in at least one of: species of plant, type of disease, type of damage, and degree of damage.

7. The method according to claim 6 wherein determining the prediction of plant health comprises:

determining a first prediction of plant health based on the derivative of the plurality of reflectance values and the first plurality of reference reflectance values;

determining a second prediction of plant health based on the derivative of the plurality of reflectance values and the second plurality of reference reflectance values; and selecting the first prediction based on the first prediction corresponding to at least one of: a greater likelihood of health, a greater measure of confidence, and/or a lesser regression loss metric than the second prediction.

8. The method according to claim 1 wherein the spectral bases having been generated from one or more images comprising at least one image representing at least a further portion of at least one further plant, wherein optionally the plurality of spectral bases comprises at least four spectral bases.

9. The method according to claim 1 wherein generating the multispectral image comprises interpolating at least one multispectral reflectance value for a wavelength of at least one of the n multispectral channels outside of the m input multispectral channels; or the method further comprising segmenting the input multispectral image into plant and non-plant regions; wherein generating the multispectral image comprises generating the multispectral image for the plant regions.

10. The method according to claim 1 comprising:

receiving a calibration input multispectral image representing at least a portion of a calibration subject, the at least the portion of the calibration subject substantially non-reflective in one or more input multispectral channels of the m input multispectral channels; and determining, for at least one of the one or more input multispectral channels, a corresponding calibration reflectance of at least a portion of the input multispectral image representing at least the portion of the calibration subject;

wherein generating the multispectral image comprises, for the at least one of the one or more input multispectral channels, subtracting the corresponding calibration reflectance.

11. The method according to claim 1 wherein at least one of the m input multispectral channels comprises at least one wavelength in a range of about 525 nm to 575 nm, at least one wavelength in a range of about 600 nm to 700 nm, and/or at least one wavelength in a range of about 400 nm to 500 nm.

12. The method according to claim 11 wherein the m input multispectral channels comprise at least four input multispectral channels, and/or wherein the m input multispectral channels comprise no more than ten input multispectral channels.

13. The method according to claim 11 wherein receiving the input multispectral image comprises causing an imaging sensor having infrared sensitivity to capture one or more frames through one or more optical filters.

14. The method according to claim 13 wherein:

the imaging sensor comprises at least one of: an RGB imaging sensor with NIR sensitivity and a monochrome imaging sensor;

the one or more optical filters comprise a plurality of optical filters; and causing the imaging sensor to capture one or more frames comprises causing the imaging sensor to capture a plurality of frames by capturing at least one frame through each of the plurality of optical filters; optionally wherein causing the imaging sensor to capture the plurality of frames by capturing at least one frame through each of the plurality of optical filters comprises causing the plurality of optical filters to revolve through a field of view of the imaging sensor while causing the imaging sensor to capture frames.

15. The method according to claim 1 wherein generating the determination comprises:

determining, for a first spatial location of at least one of the input multispectral image and the multispectral image, that a measure of one or more reflectance values of the first spatial location at least one of: exceeds a specularity threshold and is less than non-illumination threshold; and excluding the one or more reflectance values of the first spatial location from the determination based on said determining.

16. The method according to claim 1 wherein generating the determination comprises determining the derivative based on a difference between a first reflectance value in a spectral region and a second reflectance value in the spectral region; optionally wherein the spectral region comprises a first wavelength approximately corresponding to a local maximum of reflectance with respect to wavelength and a second wavelength approximately corresponding to a local minimum of reflectance with respect to wavelength, the difference between the first and second reflectance values approximating a slope of reflectance values in the spectral region with respect to wavelength; further optionally wherein determining the derivative based on the difference between the first and second reflectance values comprises normalizing the difference based on a measure of total reflectance in the spectral region; further optionally wherein normalizing the difference based on the measure of total reflectance in the spectral region comprises determining a sum of reflectances at the first and second wavelengths and normalizing based on the sum; further optionally wherein determining the derivative comprises determining a sum comprising a reflectance value at a baseline wavelength outside of the spectral region.

17. The method according to claim 16 wherein at least the portion of at least one plant comprises at least a portion of a wheat leaf.

18. The method according to claim 17 wherein the spectral region comprises a region between approximately 570 nm and 670 nm, optionally wherein the first wavelength comprises approximately 570 nm and the second wavelength comprises approximately 670 nm, further optionally wherein determining the derivative comprises determining a sum comprising a reflectance value at a baseline wavelength comprising approximately 500 nm.

19. A computer system comprising:
one or more processors; and
a memory storing instructions which cause the one or more processors to perform operations comprising:
    performing the acts of the method according to claim 1.

* * * * *